United States Patent
Chi et al.

(10) Patent No.: US 11,306,091 B2
(45) Date of Patent: Apr. 19, 2022

(54) PROCESS FOR PRODUCING FLUORINATED COMPOUNDS USING ALCOHOL SOLVENT HAVING UNSATURATED HYDROCARBON

(71) Applicant: FUTURECHEM CO., LTD, Seoul (KR)

(72) Inventors: Dae Yoon Chi, Seoul (KR); Byoung Se Lee, Seoul (KR); So Young Chu, Seoul (KR); Hyeon Jin Jeong, Seoul (KR); Hyeon Seok Kim, Seoul (KR)

(73) Assignee: FUTURECHEM CO., LTD, Seoul (KR)

( * ) Notice: Subject to any disclaimer, the term of this patent is extended or adjusted under 35 U.S.C. 154(b) by 0 days.

(21) Appl. No.: 16/888,272

(22) Filed: May 29, 2020

(65) Prior Publication Data
US 2020/0407360 A1 Dec. 31, 2020

(30) Foreign Application Priority Data
Jun. 25, 2019 (KR) .................. 10-2019-0075528

(51) Int. Cl.
| | | |
|---|---|---|
| C07D 471/08 | (2006.01) | |
| C07D 417/04 | (2006.01) | |
| C07C 209/74 | (2006.01) | |
| C07C 43/225 | (2006.01) | |
| C07H 1/00 | (2006.01) | |

(52) U.S. Cl.
CPC .......... *C07D 471/08* (2013.01); *C07C 43/225* (2013.01); *C07C 209/74* (2013.01); *C07D 417/04* (2013.01); *C07H 1/00* (2013.01)

(58) Field of Classification Search
CPC ............... C07D 471/08; C07D 417/04; C07C 43/225; C07C 209/74; C07H 1/00
USPC .................................................... 536/28.54
See application file for complete search history.

(56) References Cited

U.S. PATENT DOCUMENTS

| | | | |
|---|---|---|---|
| 2008/0171863 A1* | 7/2008 | Moon ................ | C07B 59/00 536/28.53 |
| 2017/0197912 A1 | 7/2017 | Zhou et al. | |

FOREIGN PATENT DOCUMENTS

| | | |
|---|---|---|
| CN | 108794286 | 11/2018 |
| KR | 10-0789847 | 6/2006 |
| KR | 10-1605291 | 3/2016 |

OTHER PUBLICATIONS

Masada et al. A Selective Synthesis of Hindered 1-Adamantyl t-Alkyl Ether. Nippon Kagaku Kaishi 5:508-512, 1996 (also including machine English translation of section 4. Conclusions) (Year: 1996).*

Kiesewetter et al. Utility of azetidinium methanesulfonates for radiosynthesis of 3-[18F]fluoropropyl amines. J Label Compd Radiopharm 2004; 47: 953-969. (Year: 2004).*
Billaud et al. (2017) "Micro-flow photosynthesis of new dienophiles for inverse-electron-demand Diels-Alder reactions. Potential applications for pretargeted in vivo PET imaging," Chemical Science 8(2): 1251-1258.
Extended European Search Report, dated Oct. 28, 2020, corresponding to European Patent Application No. 20178100.2, 11 pages.
Fang et al. (2017) "Synthesis, biological evaluation, and molecular dynamics (MD) simulation studies of three novel F-18 labeled and focal adhesion kinase (FAK) targeted 5-bromo pyrimidines as radiotracers for tumor," European Journal of Medicinal Chemistry 127: 493-508.
Kang et al. (Apr. 2019) "Bis-triethylene Glycolic Crown-5-calix[4]arene: A Promoter of Nucleophilic Fluorination Using Potassium Fluoride," Organic Letters 21(9):3062-3066.
Ono et al. (2011) "Novel $^{18}$F-Labeled Benzofuran Derivatives with Improved Properties for Positron Emission Tomography (PET) Imaging of [beta]-Amyloid Plaques in Alzheimer's Brains," Journal of Medicinal Chemistry 54(8):2971-2979.
Paramanik et al. (2015) "Catalytic nucleophilic fluorination by an imidazolium ionic liquid possessing trialkylphosphine oxide functionality," Journal of Fluorine Chemistry 178: 47-55.
Sachin et al. (2011) "An efficient synthesis of ([$^{18}$F]fluoropropyl)quinoline-5,8-diones by rapid radiofluorination-oxidative demethylation," Tetrahedron 67(10): 1763-1767.
Taher et al. (2017) "Pyrene-Tagged Ionic Liquids: Separable Organic Catalysts for $S_N2$ Fluorination," Organic Letters 19(13): 3342-3345.
Ametamey et al. (2008) "Molecular Imaging with PET," Chem. Rev. 108(5): 1501-1516.
Couturier et al. (2004) "Fluorinated tracers for imaging cancer with positron emission tomography," Eur. J. Nucl. Med. Mol. I. 31(8): 1182-1206.
Elsinga (2002) "Radiopharmaceutical chemistry for positron emission tomography," Methods. 27: 208-217.
Kilbourn et al. (1984) "A Simple $^{18}$O Water Target for $^{18}$F Production," Appl. Radiat. Isot. 35(7): 599-602.
Kim et al. (2006) "A New Class of $S_N2$ Reactions Catalyzed by Protic Solvents: Facile Fluorination for Isotopic Labeling of Diagnostic Molecules," J. Am. Chem. Soc. 128(50): 16394-16397.
Lasne et al. (2002) "Chemistry of β+-Emitting Compounds Based on Fluorine-18," Top. Curr. Chem. 222: 201-258.
Lee et al. (2007) "One-step high-radiochemical-yield synthesis of [$^{18}$F]FP-CIT using a protic solvent system," Nucl. Med. Biol. 34: 345-351.
Lee et al. (2007) "Simple and highly efficient synthesis of 3'-deoxy-3'-[$^{18}$F] fluorothymidine using nucleophilic fluorination catalyzed by protic solvent," Eur. J. Nucl. Med. Mol. Imaging. 34: 1406-1409.

(Continued)

*Primary Examiner* — Yih-Horng Shiao
(74) *Attorney, Agent, or Firm* — Leydig, Voit & Mayer, Ltd.

(57) ABSTRACT

The present invention relates to a process for producing an organofluoro compound including [$^{18}$F]fluorine, and by using a solvent represented by Formula 1 in nucleophilic fluorination reaction, an organofluoro compound may be prepared at a high yield. In addition, since the solvent has very excellent solubility for a precursor compound, the solvent is suitable for the automated synthesis of $^{18}$F-labeled radiopharmaceuticals.

8 Claims, No Drawings

(56) References Cited

OTHER PUBLICATIONS

Lee et al. (2008) "Comparison of synthesis yields of 3'-deoxy-3'-[$^{18}$F] fluorothymidine by nucleophilic fluorination in various alcohol solvents," J. Label. Compd. Radiopharm. 51: 80-82.
Levin (2005) "Primer on molecular imaging technology," Eur. J. Med. Mol. Imaging. 32(14): S325-S345.
Miller et al. (2008) "Synthesis of $^{11}$C, $^{18}$F, $^{15}$O, and $^{13}$N Radiolabels for Positron Emission Tomography," Angew. Chem. Int. Ed. 47: 8998-9033.
Notice of Preliminary Rejection with English translation, dated Aug. 21, 2019, corresponding to Korean Patent Application No. 10-2019-0075528, 6 pp.
Notice of Allowance with English translation, dated Dec. 17, 2019, corresponding to Korean Patent Application No. 10-2019-0075528, 6 pp.
Okarvi (2001) "Recent progress in fluorine-18 labelled peptide radiopharmaceuticals," Eur. J. Nucl. Med. 28(7): 929-938.
Phelps (2000) "Positron emission tomography provides molecular imaging of biological processes," Proc. Natl. Acad. Sci. USA. 97(16): 9226-9233.
Suehiro et al. (2007) "Investigation of the role of the base in the synthesis of [$^{18}$F]FLT," Appl. Radiat. Isot. 65: 1350-1358.
Welch et al. (2003) "Description," *Handbook of Radiopharrmaceuticals: Radiochemistry and Applications,* John Wiley & Sons, 2 pp.
Willmann et al. (2008) "Molecular imaging in drug development," Nat. Rev. Drug Discovery 7: 591-607.

\* cited by examiner

PROCESS FOR PRODUCING FLUORINATED COMPOUNDS USING ALCOHOL SOLVENT HAVING UNSATURATED HYDROCARBON

CROSS-REFERENCE TO RELATED APPLICATIONS

This patent application claims the benefit of priority from Korean Patent Application No. 10-2019-0075528, filed on Jun. 25, 2019 the content of which is incorporated herein by reference.

TECHNICAL FIELD OF THE INVENTION

The present invention relates to a process for producing a fluorinated compound coupled with fluorine-18 using an alcohol solvent having an unsaturated hydrocarbon group.

BACKGROUND OF THE INVENTION

In contrast to imaging technology such as magnetic resonance imaging (MRI) and computed tomography (CT) that provides anatomical images, positron emission tomography (PET) is technique for detecting biochemical changes in the human body using a molecular probe coupled with a radioactive isotope emitting gamma rays. Accordingly, the early diagnosis of a disease, whether the disease has recurred, and the effects of therapy, which were previously unverifiable through visual means, may now be verified. Since the radioactive isotope used in PET emits gamma rays having a short half-life and high penetrating ability and sensitivity, a trace amount is used at a level yielding low radiation exposure and no toxicity. If a compound targeting a specific disease is labeled with a positron-emitting radioactive isotope, a PET radiopharmaceutical for diagnosing the disease is obtained. Through PET radiopharmaceuticals for various diseases, the diagnostic images of cancers, cardiovascular disease, brain diseases, etc. may be obtained (Non-patent document 1. M. Ametamey, M. Honer, P. A. Schubiger, Chem. Rev. 2008, 108, 1501-1516.; J. K. Willmann, N. van Bruggen, L. M. Dinkelborg, S. S. Gambhir, Nat. Rev. Drug Discovery 2008, 591-607.; P. W. Miller, N. J. Long, R. Vilar, A. D. Gee, Angew. Chem. Int. Ed. 2008, 47, 8998-9033.; M. E. Phelps, Proc. Natl. Acad. Sci. USA 2000, 97, 9226-9233.; C. S. Levin, Eur. J. Med. Mol. Imaging 2005, 32, S325-S345).

Among various positron-emitting radioactive isotopes, fluorine-18 has a half-life of 110 minutes which is suitable for the synthesis and use of radiopharmaceuticals, and may be easily produced at high capacity using a cyclotron. In addition, since fluorine-18 has low emission energy and high specific activity, it has the merits of good image resolution, and is therefore the most widely used radionuclide (Non-patent document 2. M.-C. Lasne, C. Perrio, J. Rouden, L. Barre, D. Roeda, F. Dolle, C. Crouzel, Top. Curr. Chem. 2002, 222, 201-258.; C. Olivier, L. Andre´, C. Jean-Franc, ois, V. Jean-Philippe, R. Pierre, H. Roland, Eur. J. Nucl. Med. Mol. I. 2004, 31, 1182-1206.; P. H. Elsinga, Methods 2002, 27, 208-217.; M. J. Welch, C. S. Redvanly, Handbook of Radiopharmaceuticals, Radiochemistry and Applications, John Wiley & Sons, 2003.; M. R. Kilbourn, J. T. Hood, M. J. Welch, Appl. Radiat. Isot. 1984, 35, 599-602).

While fluorine-18 is generally used in [$^{18}$F]fluoride anion form, since the [$^{18}$F]fluoride anion is very stable and has low reactivity, the nucleophilic [$^{18}$F]fluorination of an organic compound is not easy. In addition, since the [$^{18}$F]fluoride makes a strong hydrogen bond with protic hydrogen to reduce nucleophilicity, the reaction thereof is typically performed under anhydrous conditions.

Generally, in order to increase the reactivity of [$^{18}$F]fluoride anions in nucleophilic fluorination reaction, an excessive amount of a phase transfer catalyst and a polar aprotic solvent are used. However, the reactivity of a base which is necessarily added also increases, leading to the unfavorable outcome of various by-products. In order to compensate for the degradation in yield of an organofluoro product due to the formation of by-products, a precursor compound is used in an even greater amount, which becomes a problem in making product separation (Non-patent document 3. S. M. Okarvi, Eur. J. Nucl. Med. 2001, 28, 929-938.; M. Suehiro, S. Vallabhajosula, S. J. Goldsmith, D. J. Ballon, Appl. Radiat. Isot. 2007, 65, 1350-1358).

Since an alcohol solvent, which is a protic solvent, forms a strong hydrogen bond and largely reduces the nucleophilicity of fluoride anions, methanol, ethanol, etc. are not used in typical fluorination reactions. However, a tertiary alcohol such as t-butanol and t-amyl alcohol forms a weak hydrogen bond with fluoride anions such that the nucleophilicity thereof is relatively increased. Accordingly, the tertiary alcohol solvent suppresses the basicity of the fluoride anions and the reactivity of an excessive amount of a base, thus, largely reducing side reactions. On the contrary, the nucleophilicity of the fluoride anions is relatively increased to make a nucleophilic fluorination reaction possible (Non-patent document 4. D. W. Kim, D. S. Ahn, Y. H. Oh, S. Lee, H. S. Kil, S. J. Oh, S. J. Lee, J. S. Kim, J. S. Ryu, D. H. Moon, D. Y. Chi. J. Am. Chem. Soc. 2006, 128, 16394).

For [$^{18}$F]FLT, [$^{18}$F]FP-CIT, etc., which show low yield in conventional nucleophilic [$^{18}$F]fluorination reaction using an aprotic solvent, it was confirmed that yield was largely increased by using a tertiary alcohol solvent (Non-patent document 5. S. J. Lee, S. J. Oh, D. Y. Chi, B. S. Lee, J. S. Ryu, D. H. Moon, J. Label. Compd. Radiopharm. 2008, 51, 80-82.; S. J. Lee, S. J. Oh, D. Y. Chi, S. H. Kang, H. S. Kil, J. S. Kim, D. H. Moon, Nucl. Med. Biol. 2007, 34, 345-351.; S. J. Lee, S. J. Oh, D. Y. Chi, H. S. Kil, E. N. Kim, J. S. Ryu, D. H. Moon, Eur. J. Nucl. Med. Mol. Imaging. 2007, 34, 1406).

PET radiopharmaceuticals labeled with $^{18}$F (fluorine-18) are required to be produced through an automated synthesis module, and reagents and compounds used for the production are required to be used in solution forms. However, a tertiary alcohol has low solubility for dissolving organic compounds, and is therefore unfavorable in terms of being unable to dissolve most precursor compounds used for the synthesis of PET radiopharmaceuticals. This makes the actual automated synthesis of PET radiopharmaceuticals difficult, which is a factor that degrades the industrial applicability.

In order to improve the low solubility of the tertiary alcohol, attempts have been made to add another solvent or heat a solution prior to the automated synthesis of the PET radiopharmaceuticals for the dissolution, but ultimately, these attempts not only lead to decreased product yield, but also production failure.

SUMMARY OF THE INVENTION

Disclosure of the Invention

Technical Problem

An object of the present invention is to provide a process for producing an organofluoro compound labeled with $^{18}F$ by using an alcohol solvent having an unsaturated hydrocarbon group.

Technical Solution

In order to achieve the object, the present invention provides a process for producing a organofluoro compound, including reacting a compound having a leaving group (LG) and a fluoride under a solvent, wherein the solvent is represented by the following Formula 1:

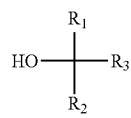

[Formula 1]

(in Formula 1, $R_1$ and $R_2$ are independently hydrogen, unsubstituted or substituted alkyl, or unsubstituted or substituted cycloalkyl; and $R_3$ is alkenyl or alkynyl).

Advantageous Effects

The process for producing an organofluoro compound according to the present invention uses an alcohol solvent having an unsaturated hydrocarbon group, and may prepare $^{18}F$-labeled radiopharmaceuticals at a higher yield when compared with a producing method using MeCN, t-butanol, t-amyl alcohol, 1-methoxy-2-methyl-2-propanol, etc., as a solvent in the related art. In addition, since a precursor compound has very excellent solubility in the alcohol solvent having an unsaturated hydrocarbon group, this alcohol solvent is suitable for the automated synthesis of the $^{18}F$-labeled radiopharmaceuticals. Also, since the alcohol solvent having an unsaturated hydrocarbon group according to the present invention dissolves well in water, additional deprotection reaction using acidic or basic aqueous solution or a purification process such as solid phase extraction of a product, performed after nucleophilic fluorination reaction may become easy.

MODE FOR CARRYING OUT THE INVENTION

Hereinafter, the present invention will be explained in detail.

Meanwhile, the example embodiments of the present invention may have various modifications, and the scope of the present invention is not limited to the example embodiments explained below. In addition, the example embodiments of the present invention are provided for the further complete explanation of the present invention to a person having average knowledge in this technical field. Further, the "comprising" of an element through the specification specify further inclusion of other elements but do not preclude another element unless otherwise indicated.

As described above, while fluorine-18 is generally used in [$^{18}F$]fluoride anion form, since the [$^{18}F$]fluoride anion is very stable and has low reactivity, it is not easy to combine with an organic compound. Accordingly, in order to increase the reactivity of the [$^{18}F$]fluoride anion, an excessive amount of a phase transfer catalyst and a polar aprotic solvent are used, but there are defects of forming various by-products. In addition, a tertiary alcohol such as t-butanol and t-amyl alcohol forms a weak hydrogen bond with the fluoride anion, and the nucleophilicity thereof is relatively increased to make nucleophilic fluorination reaction possible. However, since the solubility of an organic compound in the tertiary alcohol is low, most of precursor compounds used for synthesizing PET radiopharmaceuticals are not dissolved. This makes the actual automated synthesis of PET radiopharmaceuticals difficult and results in a factor that degrades the industrial applicability.

In order to solve such problems of nucleophilic fluorination reaction, the present invention introduces an alcohol solvent having an unsaturated hydrocarbon group and increases the solubility of precursor compounds used for synthesizing PET radiopharmaceuticals as well as the reactivity of the [$^{18}F$]fluoride anion. In conclusion, the present invention provides a method capable of replacing a solvent in the actual fields of producing a [$^{18}F$]fluoro compound and further synthesizing PET radiopharmaceuticals, and the present invention may largely contribute to the commercialization afterward.

The present invention provides a process for producing a fluoro compound, including reacting a compound having a leaving group (LG) and a fluoride under a solvent, wherein the solvent is represented by the following Formula 1:

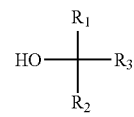

[Formula 1]

(In Formula 1, $R_1$ and $R_2$ are independently hydrogen, unsubstituted or substituted alkyl, or unsubstituted or substituted cycloalkyl; and $R_3$ is alkenyl or alkynyl).

In this case, the alkyl may be linear, branched, or cyclic alkyl.

$R_1$ and $R_2$ may form cycloalkyl together with the carbon bonded to $R_1$ and $R_2$.

The alkyl may be $C_{1-10}$ alkyl, $C_{1-8}$ alkyl, $C_{1-6}$ alkyl, $C_{1-5}$ alkyl, $C_{1-3}$ alkyl, $C_{1-2}$ alkyl, or $C_1$ alkyl.

The cycloalkyl may be $C_{3-10}$ cycloalkyl, $C_{4-9}$ cycloalkyl, $C_{5-8}$ cycloalkyl, $C_{6-8}$ cycloalkyl, or $C_{5-6}$ cycloalkyl.

$R_3$ may be alkenyl or alkynyl.

The alkenyl may be $C_{2-10}$ alkenyl, $C_{2-8}$ alkenyl, $C_{2-6}$ alkenyl, $C_{2-4}$ alkenyl, or $C_2$ alkenyl.

The alkynyl may be $C_{2-10}$ alkynyl, $C_{2-8}$ alkynyl, $C_{2-6}$ alkynyl, $C_{2-4}$ alkynyl, or $C_2$ alkynyl.

The alkenyl and alkynyl include a direct linkage with unsaturated carbon or linkage with unsaturated carbon via alkylene.

For example, if $R_3$ is alkenyl, $R_3$ may be represented by the following Formula 10:

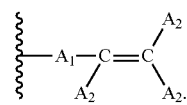

[Formula 10]

If $R_3$ is alkynyl, $R_3$ may be represented by the following Formula 11:

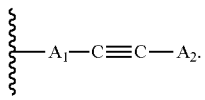

[Formula 11]

In this case, $A_1$ is $C_{0-4}$ alkylene; and each $A_2$ is independently hydrogen, linear or branched $C_{1-10}$ alkyl, linear or branched $C_{1-8}$ alkyl, linear or branched $C_{1-6}$ alkyl, linear or branched $C_{1-3}$ alkyl, or linear or branched $C_{1-2}$ alkyl.

Preferably, $R_1$ and $R_2$ may be independently hydrogen, unsubstituted or halogen-substituted alkyl, or unsubstituted or halogen-substituted cycloalkyl.

Also, preferably, $R_1$ and $R_2$ may be independently hydrogen, unsubstituted or substituted $C_{1-10}$ alkyl, or unsubstituted or substituted $C_{1-10}$ cycloalkyl.

Further preferably, $R_1$ and $R_2$ may be independently hydrogen, methyl groups, or ethyl groups; and $R_3$ may be ethenyl or ethynyl.

In addition, the fluoride may be a [$^{18}$F]fluoride.

In this case, the [$^{18}$F]fluoride may be provided from a fluoride salt including a [$^{18}$F]fluoride. The fluoride salt may use an alkali metal fluoride salt including lithium, sodium, potassium, rubidium and cesium; an alkaline earth fluoride salt including magnesium, calcium, strontium and barium; a tetraalkylammonium fluoride or tetraalkylphosphonium fluoride salt, etc., and any salt form well-known may be used without limitation.

The fluoride anions included in the fluoride salt may be trapped in a column or cartridge filled with an ion exchange solid phase, and preferably, may be entrapped using QMA (Waters) or Chromafix (Macherey-Nagel). The fluoride anions including the [$^{18}$F]fluoride trapped in the column or cartridge may be eluted by flowing a solution in which any one selected from a tetraalkylammonium salt, a tetraalkylphosphonium salt, and a cryptand-potassium salt through the cartridge. Preferably, a solution in which any one selected from a tetrabutylammonium salt, and a cryptofix 222-potassium salt may be made to flow in the cartridge for eluting the fluoride anions.

Further, the leaving group (LG) may include a halo group, a group represented by the following Formula 2, or a heterocarbocycle capable of arising ring-opening reaction:

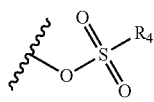

[Formula 2]

(in Formula 2, $R_4$ is hydrogen, liner or branched, unsubstituted or substituted $C_{1-10}$ alkyl, unsubstituted or substituted $C_{6-10}$ aryl, or unsubstituted or substituted $C_{6-10}$ aryl $C_{1-10}$ alkyl, and the substituted alkyl, aryl and aryl alkyl are each independently alkyl, aryl and aryl alkyl substituted with one or more substituents selected from the group consisting of linear or branched $C_{1-5}$ alkyl, linear or branched $C_{1-5}$ alkoxy, a halo group, an amine group, a nitro group, a nitrile group and a hydroxyl group).

Preferably, in Formula 2, $R_4$ may be hydrogen, linear or branched, unsubstituted or substituted $C_{1-5}$ alkyl, a unsubstituted or substituted phenyl group, or unsubstituted or substituted phenyl $C_{1-3}$ alkyl, and the substituted alkyl, phenyl and phenyl alkyl may be each independently alkyl, phenyl and phenyl alkyl substituted with one or more substituents selected from the group consisting of linear or branched $C_{1-3}$ alkyl, linear or branched $C_{1-3}$ alkoxy, a halo group, an amine group, a nitro group, a nitrile group and a hydroxyl group.

Formula 2 may be, in some embodiment,

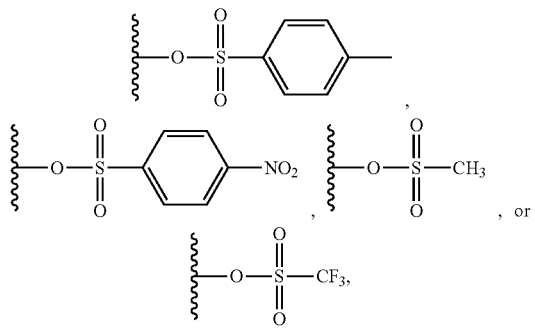

but is not limited thereto.

In addition, the halo group may be —F, —Cl, —Br, or —I.

In case of forming a leaving group by ring-opening reaction, the leaving group is, for example, cyclized while including O, S, $OSO_3$, $SO_3$, or $N^+R_6R_7$ in a precursor state and then is transformed into a type such as OH, SH, $OSO_3H$, $SO_3H$, $NR_6R_7$, etc. by ring-opening during the reaction.

Further, the reaction time is not specifically limited but in some embodiments, may be performed for 5 minutes to 60 minutes, may be performed for 5 minutes to 55 minutes, may be performed for 5 minutes to 50 minutes, may be performed for 5 minutes to 45 minutes, may be performed for 5 minutes to 40 minutes, may be performed for 5 minutes to 35 minutes, may be performed for 5 minutes to 30 minutes, may be performed for 5 minutes to 25 minutes, may be performed for 5 minutes to 20 minutes, may be performed for 5 minutes to 15 minutes, or may be performed for 5 minutes to 10 minutes. In this case, if the reaction time is less than 5 minutes, there are problems of insufficiently producing a target $^{18}$F-labeled radiopharmaceutical, that is, a fluorinated compound, and if the reaction time is greater than 60 minutes, the reaction is induced for a time longer than required for completing the reaction, and it is waste of time.

In addition, the reaction temperature is not specifically limited, but in some embodiments, may be performed in a temperature range of 60° C. to 160° C., may be performed in a temperature range of 60° C. to 150° C., may be performed in a temperature range of 70° C. to 160° C., may be performed in a temperature range of 70° C. to 150° C., may be performed in a temperature range of 80° C. to 140° C., may be performed in a temperature range of 90° C. to 130° C., may be performed in a temperature range of 90° C. to 160° C., may be performed in a temperature range of 95° C. to 125° C., may be performed in a temperature range of 95° C. to 120° C., may be performed in a temperature range of 95° C. to 115° C., may be performed in a temperature range of 100° C. to 120° C., may be performed in a temperature range of 100° C. to 115° C., may be performed in a temperature range of 100° C. to 125° C., may be performed in a temperature range of 100° C. to 130° C., may be performed in a temperature range of 105° C. to 120° C., or may be performed in a temperature range of 100° C. to 110° C. In this case, if the reaction temperature is less than 60° C., there are problems of insufficiently inducing the reaction, and if the reaction temperature is greater than 160° C., by-products are produced due to the high temperature more than needs, and the yield of a target $^{18}$F-labeled radiopharmaceutical may be degraded.

Further, the fluoro compound may be [$^{18}$F]fluoropropyl-carbomethoxytropane ([$^{18}$F]FP-CIT) represented by the following Formula 3:

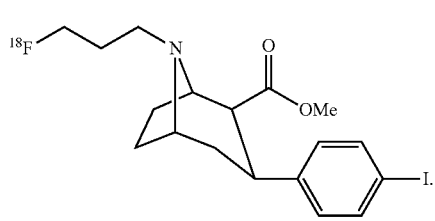
[Formula 3]

The fluoro compound may be [$^{18}$F]fluorodeoxyglucose ([$^{18}$F]FDG) represented by the following Formula 4:

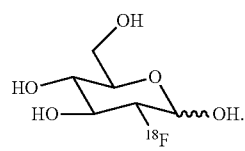
[Formula 4]

The fluoro compound may be [$^{18}$F]fluoro-L-thymidine ([$^{18}$F]FLT) represented by the following Formula 5:

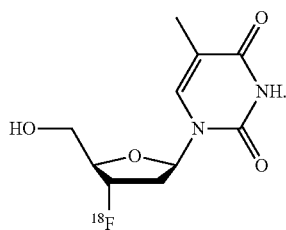
[Formula 5]

The fluoro compound may be 6-(3-[$^{18}$F]fluoro-2-hydroxypropyloxy)-2-(2-(4-methylamino)pyridine-5-yl)benzothiazol ([$^{18}$F]FC119S) represented by the following Formula 6:

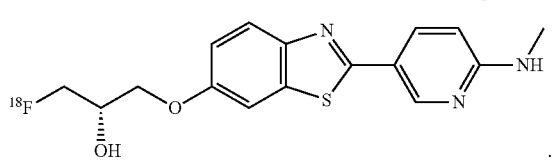
[Formula 6]

The fluoro compound may be 2-(2-(2-[$^{18}$F]fluoroethoxy)ethoxy)ethyl azide represented by the following Formula 7:

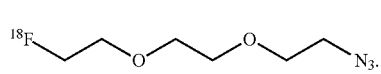
[Formula 7]

The fluoro compound may be 2-(3-([$^{18}$F]fluoro)propoxy) naphthalene represented by the following Formula 8:

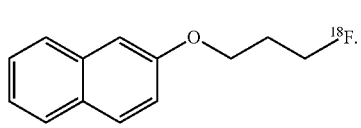
[Formula 8]

The fluoro compound may be 2-(2-([$^{18}$F]fluoro)propoxy) naphthalene represented by the following Formula 9:

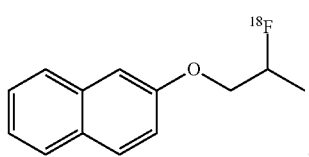
[Formula 9]

An embodiment of the process for producing the fluoro compound provided in the present invention is as Reaction 1 below.

[Reaction 1]

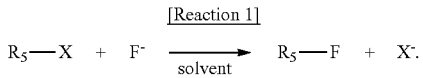

In Reaction 1, $R_5$—X corresponds to an organic compound and may include all optional known materials used in nucleophilic fluorination reaction. X is the aforementioned leaving group (LG).

$R_5$ may be an aliphatic compound. In this case, the aliphatic compound includes all of a chain type compound without a ring, a ring type compound having a ring structure, a saturated compound, and an unsaturated compound. In an embodiment, the aliphatic compound may be an organic compound of $C_{1-100}$, an organic compound of $C_{1-50}$, an organic compound of $C_{1-60}$, an organic compound of $C_{1-40}$, or an organic compound of $C_{1-20}$.

In this case, one or more carbon atoms constituting the organic compound may be substituted with one or more heteroatoms selected from the group consisting of N, O and S.

In addition, one or more hydrogen atoms constituting the organic compound may be substituted with one or more substituents below: alkyl, alkoxy, cycloalkyl, aryl, heterocycloalkyl, heteroaryl, cycloalkyl-alkyl, aryl-alkyl, heterocycloalkyl-alkyl, heteroaryl-alkyl, cycloalkyloxy, aryloxy, heterocycloalkyloxy, heteroaryloxy, halogen, hydroxyl, nitro, nitrile (cyano), oxo (=O), carbonyl, etc. In this case, the substituent may be saturated or unsaturated. In this case, the unsaturated means a case of including one or more C=C bonds, or one or more C≡C bonds, and a case of including both a C=C bond and a C≡C bond is included.

In addition, $R_5$—X may be a type in which a leaving group X is connected with sp³ carbon.

The sp³ carbon is one among carbon constituting alkyl or cycloalkyl.

The carbon of the alkyl or cycloalkyl may be substituted with one or more heteroatoms selected from the group consisting of N, O and S.

The alkyl or cycloalkyl may be substituted with aryl, heteroaryl, alkoxy, heterocycloalkyl, heteroaryl, cycloalkyl-alkyl, aryl-alkyl, heterocycloalkyl-alkyl, heteroaryl-alkyl, cycloalkyloxy, aryloxy, heterocycloalkyloxy, heteroaryloxy, halogen, hydroxyl, nitro, nitrile (cyano), oxo (=O), or carbonyl.

The cycloalkyl, aryl, heterocycloalkyl, and heteroaryl may have a bridged ring type, a fused ring type, a spiro ring type, or a ring type having a branch.

Another embodiment of the process for producing the fluoro compound provided in the present invention is as the following Reaction 2:

[Reaction 2]

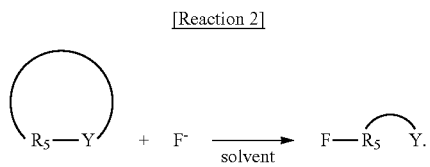

In Reaction 2, the

is carbocycle, and the carbocycle includes heterocycle or heteroaryl.

$R_5$ is the same as the aforementioned $R_5$.

Y may be one selected from the group consisting of O, S, $NR_6R_7$, $OSO_3$, and $SO_3$.

$R_6$ and $R_7$ may be each independently the same as the aforementioned $R_5$, or may be connected with methylene, oxygen, sulfur, or nitrogen to form carbocycle, and the carbocycle includes heterocycle or heteroaryl.

Also, the

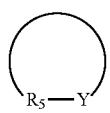

may be, for example,

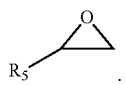

The

includes a product obtained from ring-opening reaction including an attacking process of F⁻ to $R_5$ of

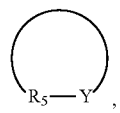

and a process of cleaving a $R_5$—Y bond.

In this case, in

Y may be present in a state of Y⁻, or may present in a state of —OH, —SH, —OSO₃H, or —SO₃H.

Another embodiment of the process for producing the fluoro compound provided in the present invention is as the following Reaction 3:

[Reaction 3]

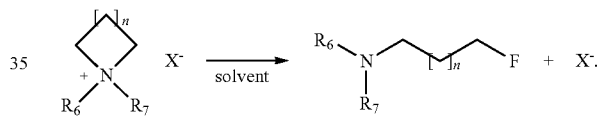

In Reaction 3, n is an integer of 0 to 6, a quaternary ammonium compound which is a starting material, corresponds to a precursor organic compound and may include all optional known materials used in nucleophilic fluorination reaction. X is the same as the aforementioned leaving group (LG).

$R_6$ and $R_7$ are each independently the same as $R_5$, and may be connected via methylene, O, S, or N to form carbocycle, and the carbocycle includes heterocycle and heteroaryl.

Particular examples of the precursor organic compounds of Reaction 1 to Reaction 3 include

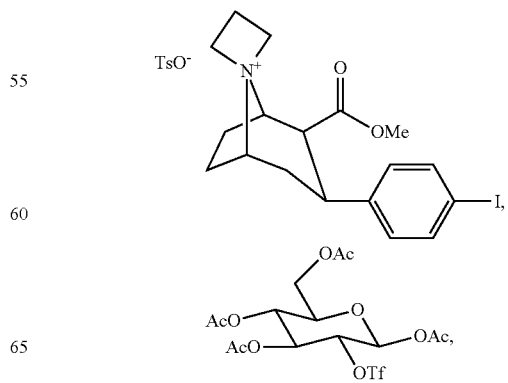

-continued

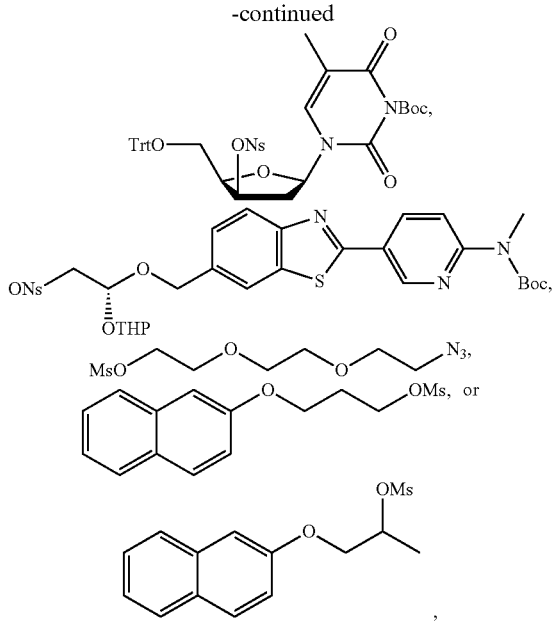

but is not limited thereto.

DETAILED DESCRIPTION OF THE INVENTION

Hereinafter, the meaning of each substituent will be explained in particular.

Alkyl

Some particular examples may include linear or branched $C_{1-20}$ alkyl, linear or branched $C_{1-15}$ alkyl, linear or branched $C_{1-10}$ alkyl, and linear or branched $C_{1-5}$ alkyl, and unsaturated alkyl including a C=C bond and/or a C≡C bond may be also included.

In addition, one or more carbon atoms constituting the alkyl may be substituted with one or more heteroatoms selected from the group consisting of N, O and S.

Alkoxy

Alkoxy may be represented by "—O-alkyl", and in this case, alkyl is the same as the above-defined alkyl.

Cycloalkyl

Some particular examples may include $C_{3-15}$ cycloalkyl, $C_{3-10}$ cycloalkyl, $C_{3-8}$ cycloalkyl, $C_{3-7}$ cycloalkyl, $C_{3-6}$ cycloalkyl, $C_{3-5}$ cycloalkyl, $C_{3-4}$ cycloalkyl, etc., and unsaturated cycloalkyl including a C=C bond and/or a C≡C bond may be also included.

Aryl

Some particular examples may include $C_{6-10}$ aryl, $C_{6-8}$ aryl, $C_6$ aryl, naphthalene, anthracene, etc.

Heterocycloalkyl

Cycloalkyl of which one or more carbon atoms are substituted with one or more heteroatoms selected from the group consisting of N, O and S corresponds to the heterocycloalkyl.

Heteroaryl

Aryl of which one or more carbon atoms are substituted with one or more heteroatoms selected from the group consisting of N, O and S corresponds to the heteroaryl.

Cycloalkyl-alkyl

Cycloalkyl-alkyl may be represented by "-alkyl-cycloalkyl", and in this case, alkyl and cycloalkyl are the same as the above-defined alkyl and cycloalkyl, respectively.

Aryl-alkyl

Aryl-alkyl may be represented by "-alkyl-aryl", and in this case, alkyl and aryl are the same as the above-defined alkyl and aryl, respectively.

Heterocycloalkyl-alkyl

Heterocycloalkyl-alkyl may be represented by "-alkyl-heterocycloalkyl", and in this case, alkyl and heterocycloalkyl are the same as the above-defined alkyl and heterocycloalkyl, respectively.

Heteroaryl-alkyl

Heteroaryl-alkyl may be represented by "-alkyl-heteroaryl", and in this case, alkyl and heteroaryl are the same as the above-defined alkyl and heteroaryl, respectively.

Cycloalkyloxy

Cycloalkyloxy may be represented by "—O-cycloalkyl", and in this case, cycloalkyl is the same as the above-defined cycloalkyl.

Aryloxy

Aryloxy may be represented by "—O-aryl", and in this case, aryl is the same as the above-defined aryl.

Heterocycloalkyloxy

Heterocycloalkyloxy may be represented by "—O-heterocycloalkyl", and in this case, heterocycloalkyl is the same as the above-defined heterocycloalkyl.

Heteroaryloxy

Heteroaryloxy may be represented by "—O-heteroaryl", and in this case, heteroaryl is the same as the above-defined heteroaryl.

Halogen may be one or more selected from —F, —Cl, —Br, and —I; hydroxyl means —OH; nitro means —$NO_2$; nitrile (cyano) means —CN; oxo means =O; and carbonyl means C=O.

In addition, the substituents including alkyl, alkoxy, cycloalkyl, aryl, heterocycloalkyl, heteroaryl, cycloalkyl-alkyl, aryl-alkyl, heterocycloalkyl-alkyl, heteroaryl-alkyl, cycloalkyloxy, aryloxy, heterocycloalkyloxy, heteroaryloxy, halogen, hydroxyl, nitro, nitrile (cyano), oxo (=O), carbonyl, etc., may be further substituted with the aforementioned substituents including alkyl, alkoxy, cycloalkyl, aryl, heterocycloalkyl, heteroaryl, cycloalkyl-alkyl, aryl-alkyl, heterocycloalkyl-alkyl, heteroaryl-alkyl, cycloalkyloxy, aryloxy, heterocycloalkyloxy, heteroaryloxy, halogen, hydroxyl, nitro, nitrile (cyano), oxo (=O), carbonyl, etc., without limitation.

Further, the present invention provides a process for producing a $^{18}$F-radiopharmaceutical through an automated synthesis module using a solution of a precursor compound dissolved in an alcohol solvent having an unsaturated hydrocarbon group. The process for producing a $^{18}$F-radiopharmaceutical has substantially the same configuration as the process for producing the fluorinated compound, and particular explanation will be omitted to avoid repeated description.

The present invention uses the compound represented by Formula 1 as a solvent in the nucleophilic fluorination reaction of a precursor compound, and since the solvent represented by Formula 1 includes an alcohol functional group, side reactions due to a base is suppressed to increase the yield of a product, and the solubility of the precursor compound is good. Since the solubility of the precursor compound is low in the conventional alcohol solvent, mixing with another solvent or heating is unfavorably required for dissolving. However, the solvent represented by Formula 1 of the present invention itself dissolves the precursor compound well, and the solvent is suitable for the synthesis of a $^{18}$F-coupled organofluoro compound, which requires an automated synthesis module. Since compounds and reagents required for the automated synthesis module are used in liquid states, if the solvent represented by Formula 1 of the present invention is used, the stable automated synthesis of a $^{18}$F-labeled organofluoro compound becomes possible. In addition, since the solvent represented by Formula 1 of the present invention is dissolved in water well, deprotection reaction using an aqueous solution or a purification process such as solid phase extraction may become easy after performing nucleophilic fluorination reaction.

In order to verify the effects of the present invention, a case of using an alcohol solvent having an unsaturated hydrocarbon group of the present invention was compared to cases using t-butanol and t-amyl alcohol as solvents, and it was confirmed that organofluorinated compound could be produced at a relatively markedly excellent yield in the present invention (see Examples and Experimental Examples).

Hereinafter, the present invention will be explained in detail referring to examples and experimental examples.

However, the examples and experimental examples are only for the illustration of the present invention, and the present invention is not limited thereto.

<Example 1> Preparation of [$^{18}$F]fluoropropylcarbomethoxytropane ([$^{18}$F]FP-CIT) Using "2-methyl-3-butene-2-ol" as a Solvent

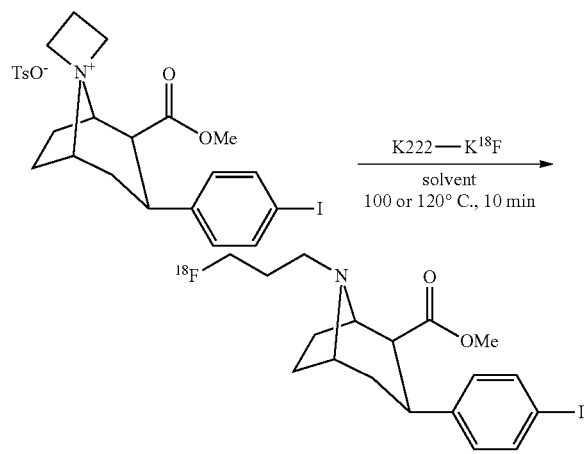

An aqueous solution in which [$^{18}$F]fluoride (1-10 mCi) ions were dissolved was passed through an ion exchange cartridge (QMA, HCO$_3$) for entrapment, and then, 3.0 ml of ethanol was passed through. A solution in which 10 mg of a kryptofix 222-potassium methanesulfonate salt (K222-KOMs salt) was dissolved in 1.0 ml of ethanol was made to flow through the cartridge which trapped the [$^{18}$F]fluoride, and a nitrogen gas was blown while heating to 100° C. to remove ethanol. 4.0 mg of a precursor compound (1'R,2'S,3'S,5'S)-3'-(4-iodophenyl)-2'-(methoxycarbonyl)spiro[azetidine-1,8'-bicyclo[3,2,1]octan]-1-ium p-toluenesulfonate) was dissolved in 0.5 ml of 2-methyl-3-butene-2-ol and then, put in a reaction vessel and reacted at 100° C. to 120° C. for 10 minutes. After the reaction, the reaction product was analyzed by radio-thin layer chromatography (radio-TLC) to obtain $^{18}$F-labeled product. The analysis results by the radio-TLC after 10 minutes are shown in [Table 1] below.

<Example 2> Preparation of [$^{18}$F]fluoropropylcarbomethoxytropane ([$^{18}$F]FP-CIT) Using "2-methyl-3-butyne-2-ol" as a Solvent

[$^{18}$F]fluoropropylcarbomethoxytropane ([$^{18}$F]FP-CIT) was prepared by the same method as in <Example 1> except for using 2-methyl-3-butyne-2-ol instead of 2-methyl-3-butene-2-ol as the reaction solvent.

<Comparative Example 1> Preparation of [$^{18}$F] fluoropropylcarbomethoxytropane ([$^{18}$F]FP-CIT) Using "MeCN" as a Solvent

[$^{18}$F]fluoropropylcarbomethoxytropane ([$^{18}$F]FP-CIT) was prepared by the same method as in <Example 1> except for using MeCN instead of 2-methyl-3-butene-2-ol as the reaction solvent and performing the reaction at 120° C. instead of 100° C.

<Comparative Example 2> Preparation of [$^{18}$F] fluoropropylcarbomethoxytropane ([$^{18}$F]FP-CIT) Using "t-butanol" as a Solvent

[$^{18}$F]fluoropropylcarbomethoxytropane ([$^{18}$F]FP-CIT) was prepared by the same method as in <Example 1> except for using t-butanol instead of 2-methyl-3-butene-2-ol as the reaction solvent.

<Comparative Example 3> Preparation of [$^{18}$F] fluoropropylcarbomethoxytropane ([$^{18}$F]FP-CIT) Using "10% MeCN/t-amyl Alcohol" as a Solvent

[$^{18}$F]fluoropropylcarbomethoxytropane ([$^{18}$F]FP-CIT) was prepared by the same method as in <Example 1> except for using 10% MeCN/t-amyl alcohol instead of 2-methyl-3-butene-2-ol as the reaction solvent.

<Comparative Example 4> Preparation of [$^{18}$F] fluoropropylcarbomethoxytropane ([$^{18}$F]FP-CIT) Using "1-methoxy-2-methyl-2-propanol" as a Solvent

[$^{18}$F]fluoropropylcarbomethoxytropane ([$^{18}$F]FP-CIT) was prepared by the same method as in <Example 1> except for using 1-methoxy-2-methyl-2-propanol instead of 2-methyl-3-butene-2-ol as the reaction solvent and performing the reaction at 120° C. instead of 100° C.

In Table 1 below, the kind of the solvent used, the reaction temperature, the reaction time and product yield in each of Examples 1 and 2, and Comparative Examples 1 to 4 are shown.

TABLE 1

| | Solvent | Temperature (° C.) | Time (min) | Radio-TLC (%) | Note |
|---|---|---|---|---|---|
| Example 1 | 2-methyl-3-butene-2-ol | 100 | 10 | 92 | The present invention |
| Example 2 | 2-methyl-3-butyne-2-ol | 100 | 10 | 87 | The present invention |
| Comparative Example 1 | MeCN | 120 | 10 | 11 | — |
| Comparative Example 2 | t-butanol | 100 | 10 | 56 | KR 10-0789847 |

TABLE 1-continued

| | Solvent | Temperature (° C.) | Time (min) | Radio-TLC (%) | Note |
|---|---|---|---|---|---|
| Comparative Example 3 | 10% MeCN/t-amyl alcohol | 100 | 10 | 63 | KR 10-0789847 |
| Comparative Example 4 | 1-methoxy-2-methyl-2-propanol | 120 | 10 | 11 | KR 10-1605291 |

As shown in Table 1, Comparative Example 1 showed experimental results obtained by using the MeCN solvent in general $^{18}$F-labeling reaction, and the yield of a product after 10 minutes was mere 11%. Comparative Example 2 and Comparative Example 3 showed comparative results corresponding to the prior art (KE 10-0789847), and t-butanol showed a radio-TLC yield of 56%, and in contrast, t-amyl alcohol showed a yield of 63%. However, the precursor compound was rarely dissolved in t-butanol and t-amyl alcohol at room temperature.

Comparative Example 4 showed comparative results corresponding to the prior art (KR 10-1605291), obtained by reacting using a 1-methoxy-2-methyl-2-propanol solvent, and a radio-TLC yield of 11% was shown. This yield is smaller by about five times that of the prior art (KR 10-0789847) and is a smaller level by about 8.36 times that of Example 1 of the present invention.

Example 1 and Example 2 showed experimental results obtained by using the solvent according to the present invention. The 2-methyl-3-butene-2-ol of Example 1 showed a radio-TLC yield of 92%, and the 2-methyl-3-butyne-2-ol of Example 2 showed a radio-TLC yield of 87%. Through this, it could be confirmed that relatively higher yield was obtained as synthetic results than that of the prior art.

In addition, the solvents used in Example 1 and Example 2 had characteristics of well dissolving the precursor compounds at room temperature.

That is, the solvent used in the prior arts such as t-butanol, t-amyl alcohol and 1-methoxy-2-methyl-2-propanol could not dissolve the precursor compounds at room temperature (in a range of about 20 to 25° C.). On the contrary, the 2-methyl-3-butene-2-ol and 2-methyl-3-butyne-2-ol, which were solvents used in the present invention showed characteristics of dissolving the precursor compounds at room temperature well.

In case of using commercially produced $^{18}$F-labeled radiopharmaceuticals, the synthesis is required to conduct through an automated synthesis module, and compounds, reagents, etc. are necessary to put in the automated synthesis module in liquid states. If the solubility of the precursor in a solvent is low, the injection of the precursor to an automated synthesis module in a solution state might become difficult.

Since the solvent used in the prior art may not dissolve the precursor compound well at room temperature, a mixture of the precursor compound and the solvent could be heated to prepare a temporarily dissolved solution state to be put in the automated synthesis module, but after putting the solution in the automated synthesis module, if the temperature is reduced to room temperature, the precursor compound dissolved is solidified again, resulting in blocking a tube in the module, where the solution flows, and restraining the inflowing of a sufficient amount of the precursor. As a result, the production yield of the $^{18}$F-labeled radiopharmaceutical may be markedly reduced and defects of production fail may be generated.

However, in case of dissolving the precursor compound in the solvent used in the present invention well, effects of stable production of the $^{18}$F-labeled radiopharmaceutical may be achieved.

<Example 3> Preparation of [$^{18}$F]FDG (fluorodeoxyglucose) Using "2-methyl-2-butene-2-ol" as a Solvent

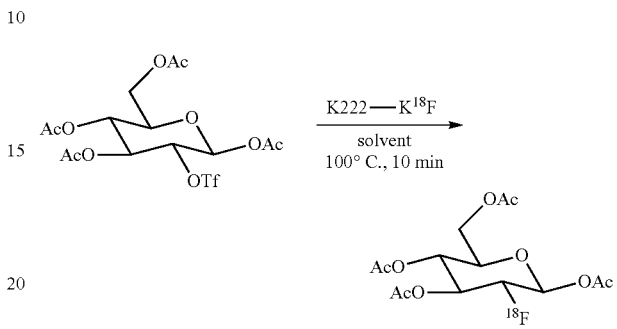

An aqueous solution in which [$^{18}$F]fluoride (1-10 mCi) ions were dissolved was passed through a cartridge filled with an ion exchange solid phase (QMA) for entrapment, and then, 3.0 ml of ethanol was passed therethrough. A solution in which 10 mg of a kryptofix 222-potassium methanesulfonate salt (K222-KOMs salt) was dissolved in 1.0 ml of ethanol was made to flow through the cartridge which trapped the [$^{18}$F]fluoride, and a nitrogen gas was blown while heating to 100° C. to remove ethanol. 25 mg of a FDG precursor compound (1,3,4,6-tetra-O-acetyl-2-O-trifluoro-methanesulfonyl-beta-D-mannopyranose) was dissolved in 0.5 ml of 2-methyl-3-butene-2-ol and then, put in a reaction vessel and reacted at 100° C. for 10 minutes. After 10 minutes, the reaction product was analyzed by radio-TLC, and the results are shown in [Table 2] below.

<Example 4> Preparation of [$^{18}$F]FDG (fluorodeoxyglucose) Using "2-methyl-2-butyne-2-ol" as a Solvent

[$^{18}$F]FDG (fluorodeoxyglucose) was prepared by the same method as in <Example 3> except for using 2-methyl-3-butyne-2-ol instead of 2-methyl-3-butene-2-ol as the reaction solvent.

The kind of the solvents used, and production yields of Example 3 and Example 4 are shown, respectively, in Table 2 below.

TABLE 2

| | Solvent | Radio-TLC (%) |
|---|---|---|
| Example 3 | 2-methyl-3-butene-2-ol | 92 |
| Example 4 | 2-methyl-3-butyne-2-ol | 90 |

As shown in Table 2,
if the 2-methyl-3-butene-2-ol solvent according to the present invention was used for producing [$^{18}$F]FDG (fluorodeoxyglucose), a very excellent radio-TLC yield of 92% could be obtained (Example 3), and if the 2-methyl-3-butyne-2-ol solvent according to the present invention was used, a very excellent radio-TLC yield of 90% could be obtained (Example 4). Accordingly, it was confirmed that if the solvent according to the present invention was used for producing [$^{18}$F]FDG (fluorodeoxyglucose), all products could be obtained at a very excellent yield of 90% or more. Through this, it was confirmed that the alcohol solvent having an unsaturated hydrocarbon group according to the present invention might be used as a very suitable solvent for the production of an organofluoro compound.

<Example 5> Preparation of [$^{18}$F]FLT (fluorothymidine) Using "2-methyl-3-butene-2-ol" as a Solvent

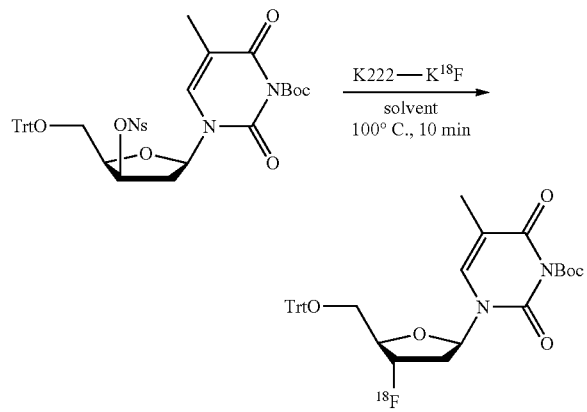

An aqueous solution in which [$^{18}$F]fluoride (1-10 mCi) ions were dissolved was passed through a cartridge filled with an ion exchange solid phase (QMA) for entrapment, and then, 3.0 ml of ethanol was passed therethrough. A solution in which 10 mg of kryptofix 222-potassium methanesulfonate salt (K222-KOMs salt) was dissolved in 1.0 ml of ethanol was made to flow through the cartridge which trapped the [$^{18}$F]fluoride, and a nitrogen gas was blown while heating to 100° C. to remove ethanol. 20 mg of a FLT precursor compound (3-N-Boc-5'-O-trityl-3'-O-nosyl-thymidine) was dissolved in 0.5 ml of 2-methyl-3-butene-2-ol and then, put in a reaction vessel and reacted at 100° C. for 10 minutes. After 10 minutes, the reaction product was analyzed by radio-TLC, and the results are shown in [Table 3] below.

<Example 6> Preparation of [$^{18}$F]FLT (fluorothymidine) Using "2-methyl-3-butyne-2-ol" as a Solvent

[$^{18}$F]FLT (fluorothymidine) was prepared by the same method as in <Example 5> except for using 2-methyl-3-butyne-2-ol instead of 2-methyl-3-butene-2-ol as the reaction solvent.

TABLE 3

|  | Solvent | Radio-TLC (%) |
| --- | --- | --- |
| Example 5 | 2-methyl-3-butene-2-ol | 92 |
| Example 6 | 2-methyl-3-butyne-2-ol | 77 |

As shown in Table 3,
if the 2-methyl-3-butene-2-ol solvent according to the present invention was used for producing [$^{18}$F]FLT (fluorothymidine), a very excellent radio-TLC yield of 92% could be obtained (Example 5), and if the 2-methyl-3-butyne-2-ol solvent according to the present invention was used, an excellent radio-TLC yield of 77% could be obtained (Example 6). Accordingly, it was confirmed that if the solvent according to the present invention was used for producing [$^{18}$F]FLT (fluorothymidine), all products could be obtained at an excellent yield. Through this, it was confirmed that the alcohol solvent having an unsaturated hydrocarbon group according to the present invention might be used as a very suitable solvent for the production of an organofluoro compound.

<Example 7> Preparation of [$^{18}$F]FC119S Using "2-methyl-3-butene-2-ol" as a Solvent

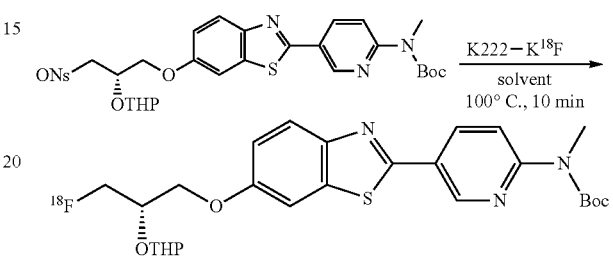

An aqueous solution in which [$^{18}$F]fluoride (1-10 mCi) ions were dissolved was passed through a cartridge filled with an ion exchange solid phase (QMA) for entrapment, and then, 3.0 ml of ethanol was passed therethrough. A solution in which 10 mg of a kryptofix 222-potassium methanesulfonate salt (K222-KOMs salt) was dissolved in 1.0 ml of ethanol was made to flow through the cartridge which trapped the [$^{18}$F]fluoride, and a nitrogen gas was blown while heating to 100° C. to remove ethanol. 5.0 mg of FC119S ((2S)-3-((2-(6-((tert-butoxycarbonyl) (methyl) amino)pyridin-3-yl)benzo[d]thiazol-6-yl)oxy)-2-((tetrahydro-2H-pyran-2-yl)oxy)propyl 4-nitrobenzenesulfonate) was dissolved in 0.5 ml of 2-methyl-3-butene-2-ol and then, put in a reaction vessel and reacted at 100° C. for 10 minutes. After 10 minutes, the reaction product was analyzed by radio-TLC, and the results are shown in [Table 4] below.

<Example 8> Preparation of [$^{18}$F]FC119S Using "2-methyl-3-butyne-2-ol" as a Solvent

[$^{18}$F]FC119S was prepared by the same method as in <Example 7> except for using 2-methyl-3-butyne-2-ol instead of 2-methyl-3-butene-2-ol as the reaction solvent.

TABLE 4

|  | Solvent | Radio-TLC (%) |
| --- | --- | --- |
| Example 7 | 2-methyl-3-butene-2-ol | 93 |
| Example 8 | 2-methyl-3-butyne-2-ol | 65 |

As shown in Table 4,
if the 2-methyl-3-butene-2-ol solvent according to the present invention was used for producing [$^{18}$F]FC119S, a very excellent radio-TLC yield of 93% could be obtained (Example 7), and if the 2-methyl-3-butyne-2-ol solvent according to the present invention was used, an excellent radio-TLC yield of 65% could be obtained (Example 8). Accordingly, it was confirmed that if the solvent according to the present invention was used for producing [$^{18}$F] FC119S, all products could be obtained at an excellent yield. Through this, it was confirmed that the alcohol solvent

\<Example 9\> Preparation of 2-(2-(2-([$^{18}$F]fluoroethoxy)ethoxy)ethyl Azide Using "2-methyl-3-butene-2-ol" as a Solvent

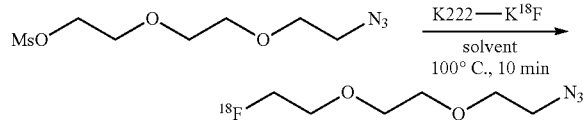

An aqueous solution in which [$^{18}$F]fluoride (1-10 mCi) ions were dissolved was passed through a cartridge filled with an ion exchange solid phase (QMA) for entrapment, and then, 3.0 ml of ethanol was passed therethrough. A solution in which 10 mg of a kryptofix 222-potassium methanesulfonate salt (K222-KOMs salt) was dissolved in 1.0 ml of ethanol was made to flow through the cartridge which trapped the [$^{18}$F]fluoride, and a nitrogen gas was blown while heating to 100° C. to remove ethanol. 5.0 mg of 2-(2-(2-azidoethoxy)ethoxy)ethyl methanesulfonate was dissolved in 0.5 ml of 2-methyl-3-butene-2-ol and then, put in a reaction vessel and reacted at 100° C. for 10 minutes. After 10 minutes, the reaction product was analyzed by radio-TLC, and a very high yield of 90% was shown.

\<Example 10\> Preparation of 2-(3-([$^{18}$F]fluoro)propoxy)naphthalene Using "2-methyl-3-butene-2-ol" as a Solvent

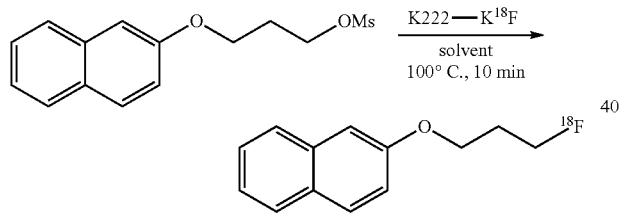

An aqueous solution in which [$^{18}$F]fluoride (1-10 mCi) ions were dissolved was passed through a cartridge filled with an ion exchange solid phase (QMA) for entrapment, and then, 3.0 ml of ethanol was passed therethrough. A solution in which 10 mg of a kryptofix 222-potassium methanesulfonate salt (K222-KOMs salt) was dissolved in 1.0 ml of ethanol was made to flow through the cartridge which trapped the [$^{18}$F]fluoride, and a nitrogen gas was blown while heating to 100° C. to remove ethanol. 5.0 mg of 3-(naphthalene-2-yloxy)propyl methanesulfonate was dissolved in 0.5 ml of 2-methyl-3-butene-2-ol and then, put in a reaction vessel and reacted at 100° C. for 10 minutes. After 10 minutes, the reaction product was analyzed by radio-TLC, and the results are shown in [Table 5] below.

\<Example 11\> Preparation of 2-(3-([$^{18}$F]fluoro)propoxy)naphthalene Using "2-methyl-3-butyne-2-ol" as a Solvent 2-(3-([$^{18}$F]fluoro)propoxy)naphthalene was prepared by the same method as in \<Example 10\> except for using 2-methyl-3-butyne-2-ol instead of 2-methyl-3-butene-2-ol as the reaction solvent.

TABLE 5

| | Solvent | Radio-TLC (%) |
|---|---|---|
| Example 10 | 2-methyl-3-butene-2-ol | 97 |
| Example 11 | 2-methyl-3-butyne-2-ol | 95 |

As shown in Table 5, if the 2-methyl-3-butene-2-ol solvent according to the present invention was used for producing 2-(3-([$^{18}$F]fluoro)propoxy)naphthalene, a very excellent radio-TLC yield of 97% could be obtained (Example 10), and if the 2-methyl-3-butyne-2-ol solvent according to the present invention was used, a very excellent radio-TLC yield of 95% could be obtained (Example 11). Accordingly, it was confirmed that if the solvent according to the present invention was used for producing 2-(3-([$^{18}$F]fluoro)propoxy)naphthalene, all products could be obtained at an excellent yield of 95% or more. Through this, it was confirmed that the alcohol solvent having an unsaturated hydrocarbon group according to the present invention might be used as a very suitable solvent for the production of an organofluoro compound.

\<Example 12\> Preparation of 2-(2-([$^{18}$F]fluoro)propoxy)naphthalene Using "2-methyl-3-butene-2-ol" as a Solvent

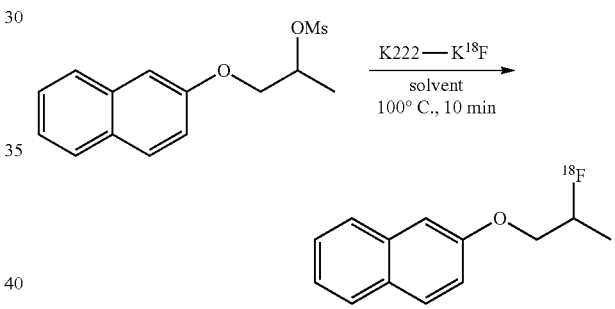

An aqueous solution in which [$^{18}$F]fluoride (1-10 mCi) ions were dissolved was passed through a cartridge filled with an ion exchange solid phase (QMA) for entrapment, and then, 3.0 ml of ethanol was passed therethrough. A solution in which 10 mg of a kryptofix 222-potassium methanesulfonate salt (K222-KOMs salt) was dissolved in 1.0 ml of ethanol was made to flow through the cartridge which trapped the [$^{18}$F]fluoride, and a nitrogen gas was blown while heating to 100° C. to remove ethanol. 10.0 mg of 1-(naphthalene-2-yloxy)propan-2-yl methanesulfonate was dissolved in 0.5 ml of 2-methyl-3-butene-2-ol and then, put in a reaction vessel and reacted at 100° C. for 10 minutes. After 10 minutes, the reaction product was analyzed by radio-TLC, and the results are shown in [Table 6] below.

\<Example 13\> Preparation of 2-(2-([$^{18}$F]fluoro)propoxy)naphthalene Using "2-methyl-3-butyne-2-ol" as a Solvent 2-(2-([$^{18}$F]fluoro)propoxy)naphthalene was prepared by the same method as in \<Example 12\> except for using 2-methyl-3-butyne-2-ol instead of 2-methyl-3-butene-2-ol as the reaction solvent.

TABLE 6

| | Solvent | Radio-TLC (%) |
|---|---|---|
| Example 12 | 2-methyl-3-butene-2-ol | 91 |
| Example 13 | 2-methyl-3-butyne-2-ol | 58 |

As shown in Table 6, if the 2-methyl-3-butene-2-ol solvent according to the present invention was used for producing 2-(2-([$^{18}$F]fluoro)propoxy)naphthalene, a very excellent radio-TLC yield of 91% could be obtained (Example 12), and if the 2-methyl-3-butyne-2-ol solvent according to the present invention was used, an excellent radio-TLC yield of 58% could be obtained (Example 13). Accordingly, it was confirmed that if the solvent according to the present invention was used for producing 2-(2-([$^{18}$F]fluoro)propoxy)naphthalene, all products could be obtained at an excellent yield. Through this, it was confirmed that the alcohol solvent having an unsaturated hydrocarbon group according to the present invention might be used as a very suitable solvent for the production of an organofluoro compound.

<Experimental Example 1> Comparison of Solubility of Precursor Compounds According to the Kind of Reaction Solvents Experiments for comparing the solubility in the 2-methyl-3-butene-2-ol solvent and 2-methyl-3-butyne-2-ol solvent according to the present invention, and the t-amyl alcohol solvent of the prior art (KE 10-0789847) were performed. Each of the precursors of FP-CIT, FDG, FLT, FMISO and FC119S in solid states was put in a vial, and 1.0 ml of each solvent was added thereto, followed by shaking at room temperature and 60° C. for 1 minutes, respectively, for dissolution. The vial was observed with the naked eye, and the observation results are summarized in [Table 7] below.

TABLE 7

| Precursor compound | Precursor amount (mg) | t-amyl alcohol (KR 10-0789847) | | 2-methyl-3-butene-2-ol (the present invention) | | 2-methyl-3-butyne-2-ol (the present invention) | |
|---|---|---|---|---|---|---|---|
| | | Room temp | 60° C. | Room temp | 60° C. | Room temp | 60° C. |
| FP-CIT | 4 | Insoluble | Dissolved | Dissolved | Dissolved | Dissolved | Dissolved |
| FDG | 20 | Insoluble | Dissolved | Dissolved | Dissolved | Dissolved | Dissolved |
| FLT | 20 | Insoluble | Insoluble | Dissolved | Dissolved | Insoluble | Dissolved |
| FMISO | 5 | Insoluble | Dissolved | Insoluble | Dissolved | Dissolved | Dissolved |
| FC119S | 5 | Insoluble | Insoluble | Dissolved | Dissolved | Dissolved | Dissolved |
| 3-(naphthalene-2-yloxy)propyl methanesulfonate | 5 | — | — | Dissolved | Dissolved | — | — |
| 1-(naphthalene-2-yloxy)propyl methanesulfonate | 10 | — | — | Dissolved | Dissolved | — | — |

As shown in Table 7, in case of using the t-amyl alcohol which was the solvent of the prior art, all precursors were insoluble at room temperature, and FLT and FC119S precursors were insoluble even heated to 60° C. The FP-CIT, FGD, and FMISO precursors, dissolved at 60° C. were precipitated again as solids if cooled to room temperature after the lapse of time.

Accordingly, since PET radiopharmaceuticals are required to be produced by an automated synthesis module, and a precursor compound is required to be used in a well-dissolved state in a reaction solvent, the t-amyl alcohol has poor solubility and is not suitable for the actual production of pharmaceuticals.

On the contrary, all precursor compounds except for FMISO were dissolved well in the 2-methyl-3-butene-2-ol according to the present invention at room temperature, and all precursor compounds except for FLT were dissolved well in the 2-methyl-3-butyne-2-ol at room temperature. If heated to 60° C., it was confirmed that all precursor compounds were dissolved in both 2-methyl-3-butene-2-ol and 2-methyl-3-butyne-2-ol. In addition, though the dissolved FLT and FMISO solutions through heating to 60° C. were cooled to room temperature, the precursor compounds were not precipitated as solids.

For the production of the $^{18}$F-radiopharmaceuticals using an automated synthesis module, precursor compounds are required to be used in solution states. Most of the precursor compounds were dissolved well in the 2-methyl-3-butene-2-ol and 2-methyl-3-butyne-2-ol at room temperature or 60° C. through heating, and the solution states were maintained after cooling to room temperature. Accordingly, different from the conventional tertiary alcohol solvent, the solvent of the present invention has excellent solubility with respect to compounds and is a more suitable solvent for producing PET radiopharmaceuticals through an automated synthesis module.

<Experimental Example 2> Automated Synthesis of [$^{18}$F]fluoropropylcarbomethoxytropane ([$^{18}$F]FP-CIT) Using "2-methyl-3-butene-2-ol" as a Solvent By applying the conditions of Example 1, the production experiment of [$^{18}$F]FP-CIT using an automated synthesis module was performed. An sCUBE module of CS CHEM Co. Ltd. was used as the automated synthesis module, and a disposable cassette and a reagent kit according to Example 1 were used. 1.5 ml of a 2-methyl-3-butene-ol solution in which 4 mg of a FP-CIT precursor was dissolved was used for the reaction, and after performing the reaction, purification was performed using a high performance liquid chromatography (HPLC) installed on the sCUBE automated synthesis module. The [$^{18}$F]FP-CIT thus separated was diluted with 40 ml of distilled water, adsorbed on a C-18 cartridge (SePak), washed with distilled water, and eluted with 2.0 ml of ethanol. This process was repeated twice further. The results of the automated synthesis experiment are summarized in Table 8 below.

TABLE 8

| Number of times | 1 | 2 | 3 |
|---|---|---|---|
| Yield (%, attenuation correction) | 32.7 | 34.0 | 35.2 |

As above, the present invention has been explained in detail referring to preferred Preparation Examples, Examples and Experimental Examples, but the scope of the present invention is not limited to the specific examples and should be interpreted by the attached claims. In addition, it is understood that various changes and modifications can be made by one ordinary skilled in the art within the spirit and scope of the present invention.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The invention claimed is:

1. A process for producing an organofluoro compound, the process comprising: reacting an organic compound having a leaving group (LG) with a fluoride in a solvent according to below Reaction 3 in a suitable condition,

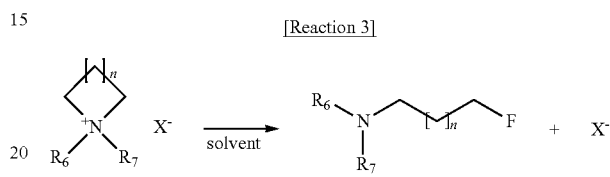

wherein the organic compound having a leaving group is

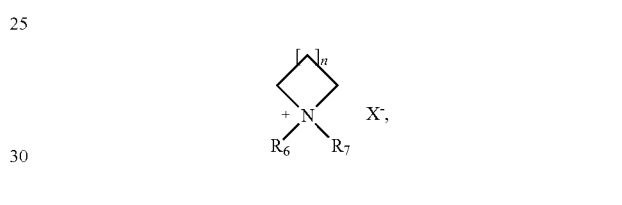

the organofluoro compound is

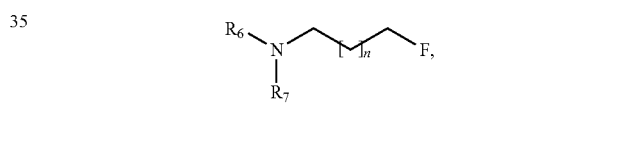

and $X^-$ is an ion generated from the leaving group, wherein $R_6$ and $R_7$ form carbocycle with N, and n is an integer of 0 to 6, wherein the solvent has the following Formula 1:

[Formula 1]

in Formula 1, $R_1$ and $R_2$ are each a methyl group; and $R_3$ is ethenyl or ethynyl, and wherein the fluoride is a [$^{18}$F] fluoride, and is provided as a component of a phase transfer catalyst.

2. The process for producing an organofluoro compound according to claim 1, wherein the reaction is performed for 5 minutes to 60 minutes.

3. The process for producing an organofluoro compound according to claim 1, wherein the reaction is performed in a temperature range of 60° C. to 160° C.

4. The process for producing an organofluoro according to claim 1, wherein the organofluoro compound is [$^{18}$F]fluoropropylcarbomethoxytropane ([$^{18}$F]FP-CIT) having the following Formula 3:

[Formula 3]

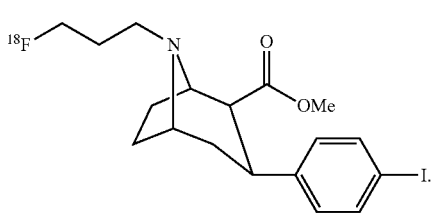

5. The process for producing an organofluoro compound according to claim 1, wherein X⁻ is an ion of a halo group or is a group having the following Formula 2:

[Formula 2]

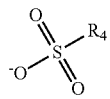

wherein in Formula 2, $R_4$ is hydrogen, linear or branched, unsubstituted or substituted $C_{1-10}$alkyl, unsubstituted or substituted $C_{6-10}$aryl, or unsubstituted or substituted $C_{6-10}$aryl $C_{1-10}$alkyl, and the substituted alkyl, aryl and aryl alkyl are each independently modified with one or more substituents selected from the group consisting of linear or branched $C_{1-5}$alkyl, linear or branched $C_{1-5}$alkoxy, a halo group, an amine group, a nitro group, a nitrile group and a hydroxyl group.

6. The process for producing an organofluoro compound according to claim 1, 1, wherein X⁻ is F, Cl, Br⁻, I⁻,

[sulfonate structures shown]

7. The process for producing an organofluoro compound according to claim 1, wherein

[azetidinium structures shown] is [tropane structure shown].

8. The process for producing an organofluoro compound according to claim 1, wherein a source of the fluoride is provided as Kryptofix 222 -K [¹⁸F].

* * * * *